United States Patent [19]
Schendel

[11] Patent Number: 5,700,263
[45] Date of Patent: Dec. 23, 1997

[54] BONE DISTRACTION APPARATUS

[76] Inventor: Stephen A. Schendel, 1001 Hermosa Way, Menlo Park, Calif. 94025

[21] Appl. No.: 664,398

[22] Filed: Jun. 17, 1996

[51] Int. Cl.$^6$ ................................................ A61B 17/58
[52] U.S. Cl. ........................... 606/57; 606/71; 606/60
[58] Field of Search ........................... 606/71, 70, 69, 606/63, 62, 58, 57, 54, 55

[56] References Cited

U.S. PATENT DOCUMENTS

| | | | |
|---|---|---|---|
| 2,333,033 | 10/1943 | Mraz | 606/57 |
| 3,604,414 | 9/1971 | Borges | 606/71 |
| 3,680,553 | 8/1972 | Seppo | 606/71 |
| 3,900,025 | 8/1975 | Barnes et al. | 606/71 |
| 4,096,857 | 6/1978 | Cramer et al. | 606/71 |
| 4,157,715 | 6/1979 | Westerhoff | |
| 4,475,546 | 10/1984 | Patton | 606/71 |
| 4,615,338 | 10/1986 | Ilizarov et al. | 606/58 |
| 5,129,903 | 7/1992 | Luhr et al. | 606/71 |
| 5,364,396 | 11/1994 | Robinson et al. | 606/53 |
| 5,466,261 | 11/1995 | Richelsoph | |

*Primary Examiner*—Guy V. Tucker
*Attorney, Agent, or Firm*—Burns, Doane, Swecker & Mathis, LLP

[57] ABSTRACT

A distraction device for osteosynthesis includes a first member which is telescopically housed within a second member. The first and second members are attached to first and second bone segments, respectively. The device includes a ratchet wheel having teeth which engage teeth of the first member. Rotation of the ratchet wheel cause the first member to telescopically extend from its second member housing in an arcuate path.

9 Claims, 6 Drawing Sheets

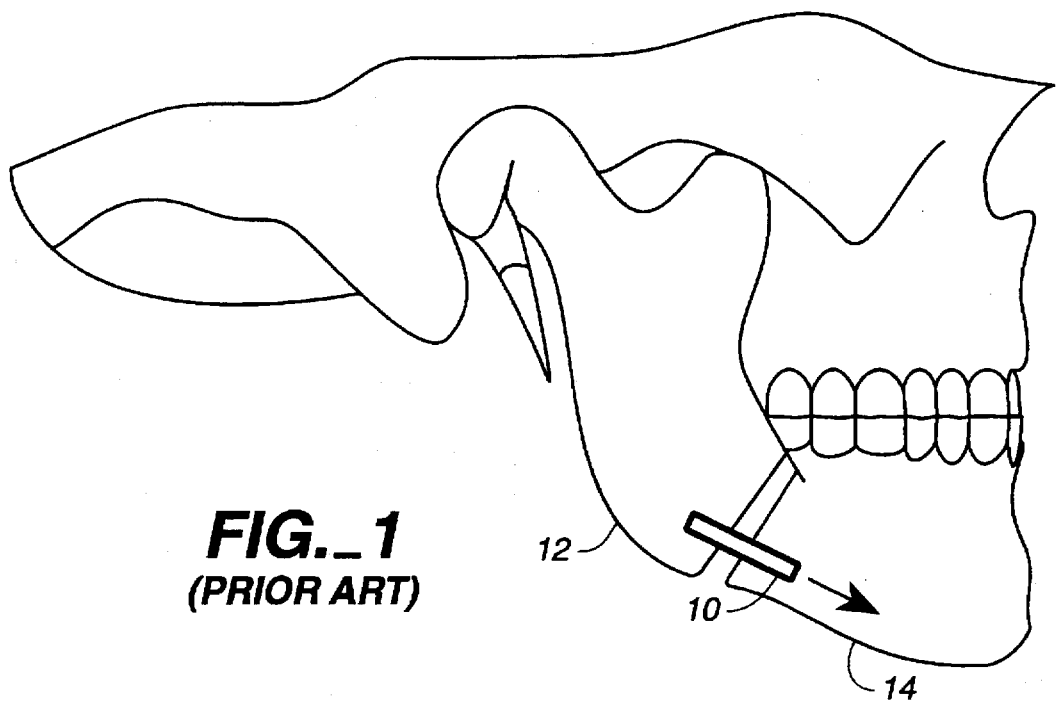
FIG._1
*(PRIOR ART)*
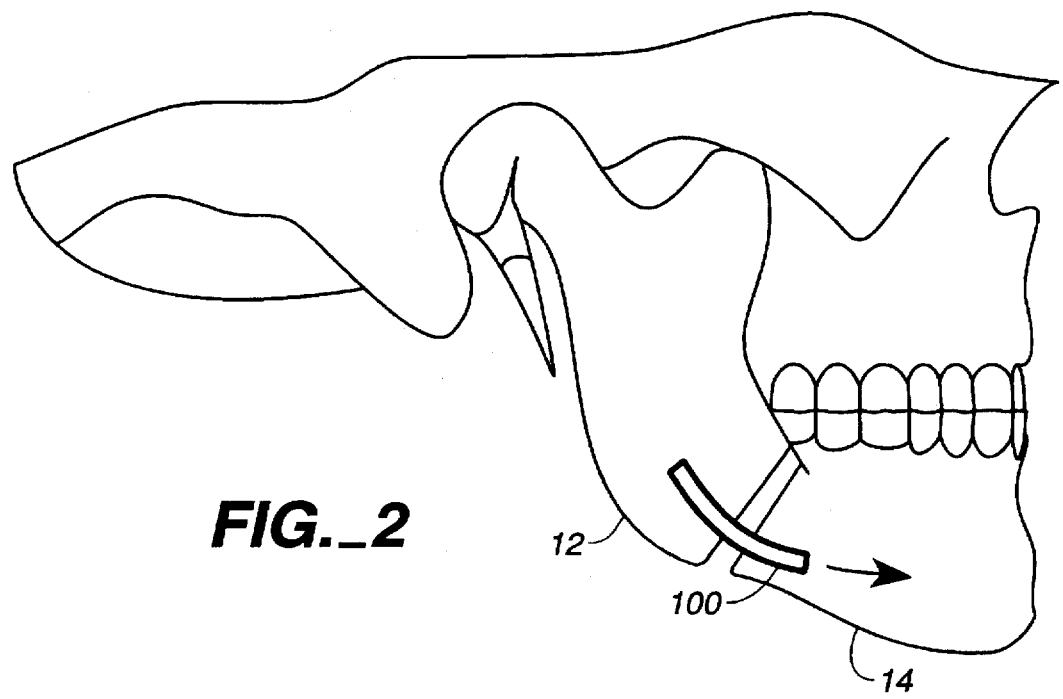
FIG._2

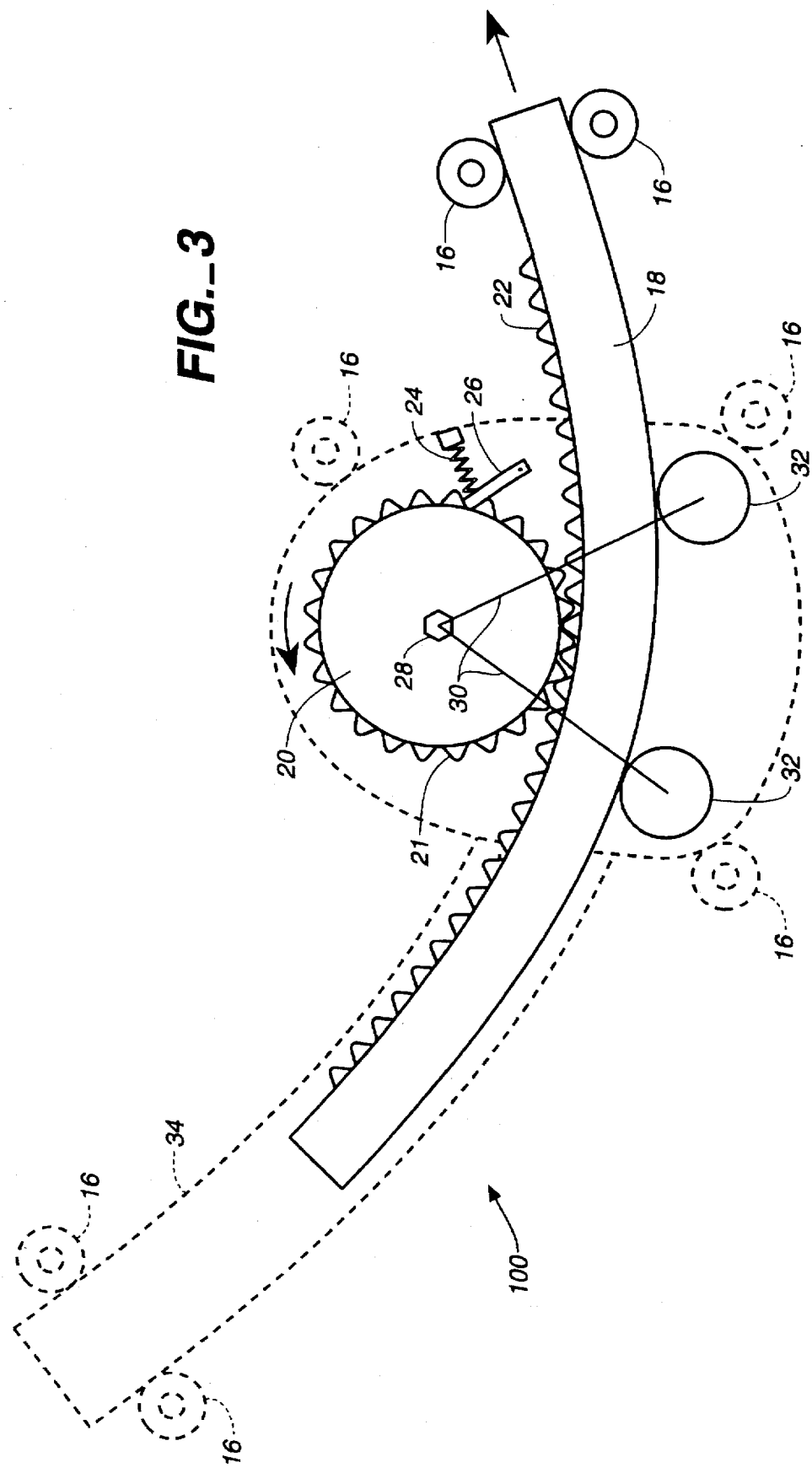

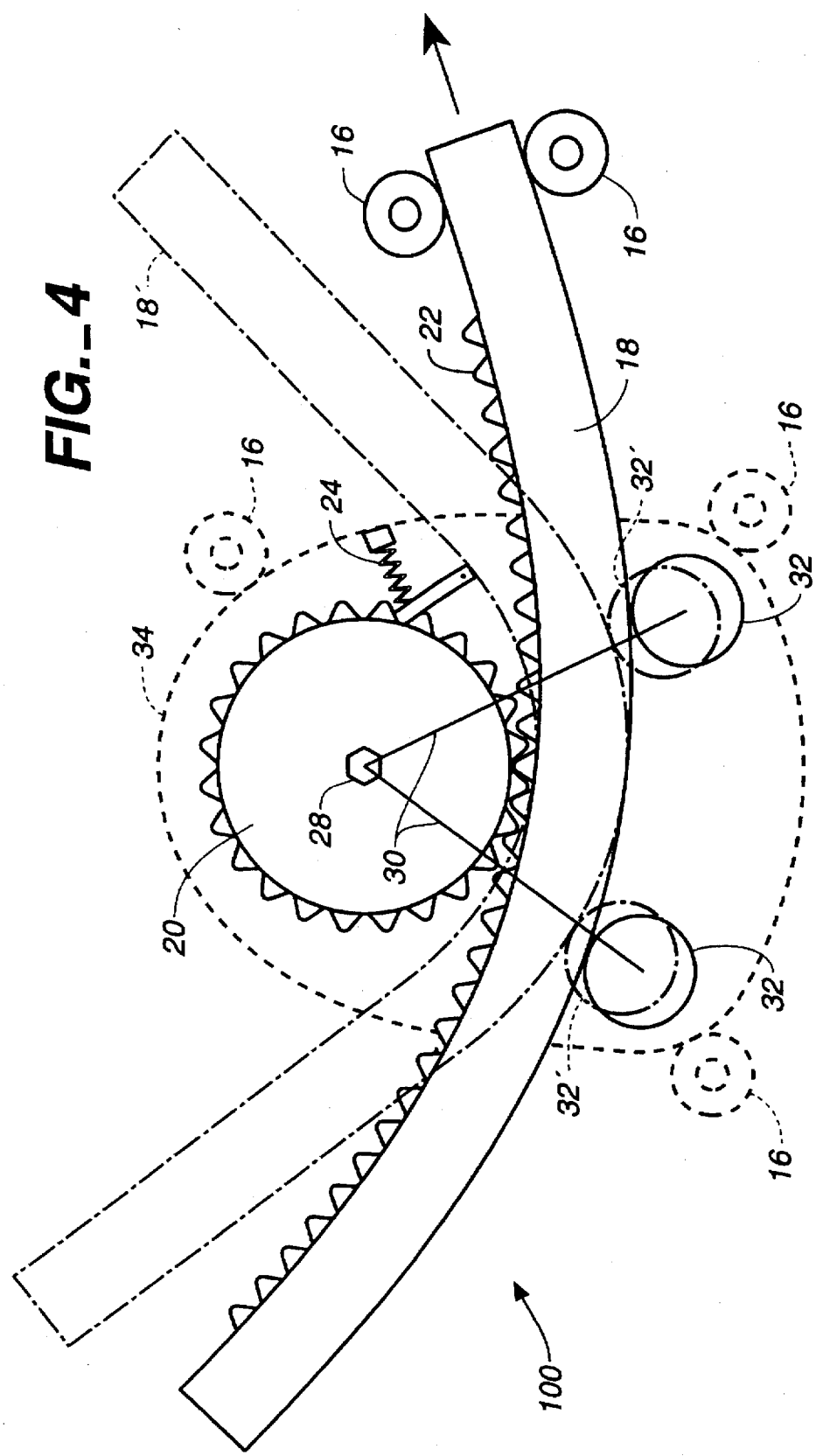
FIG._4

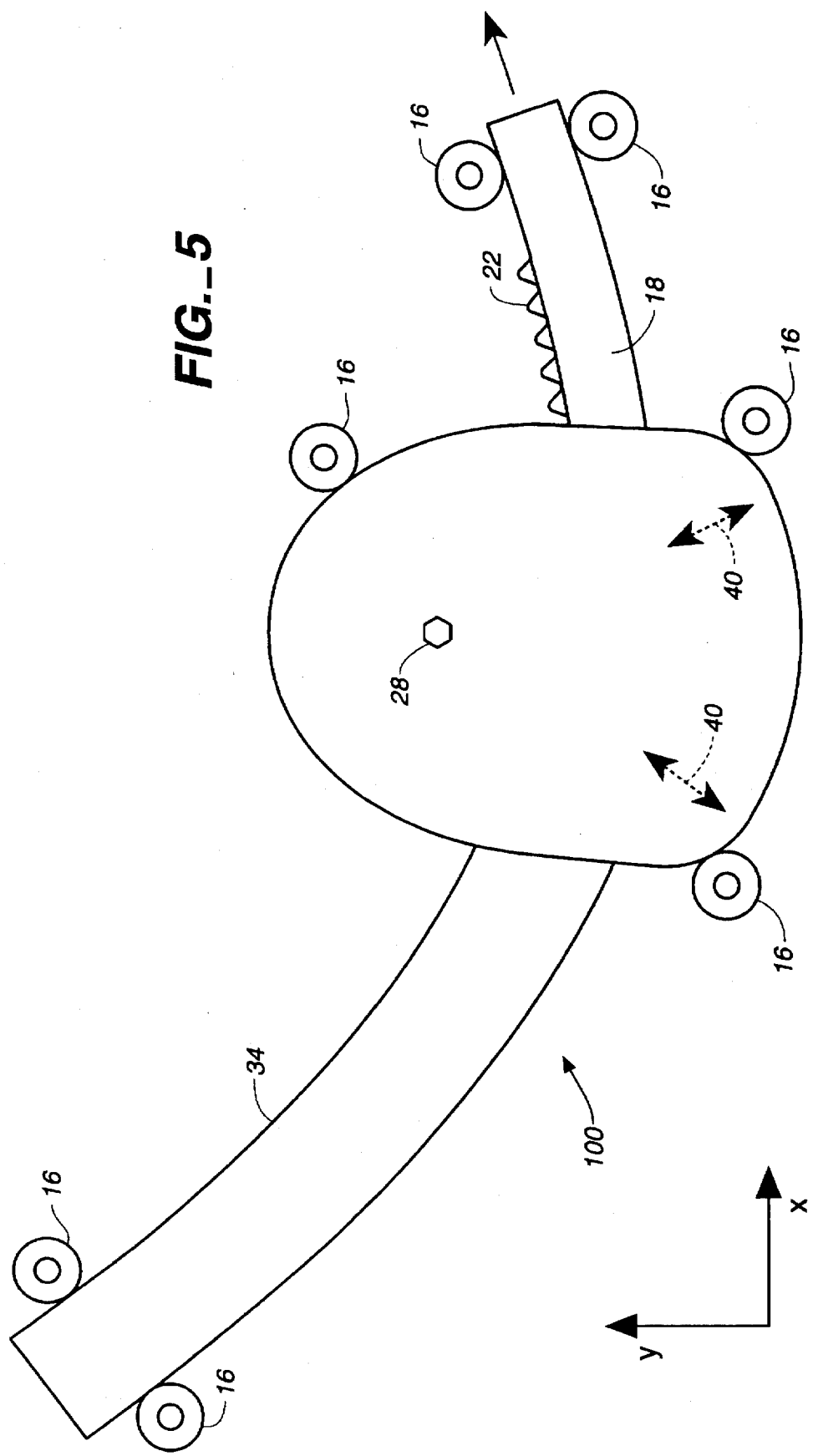
FIG._5

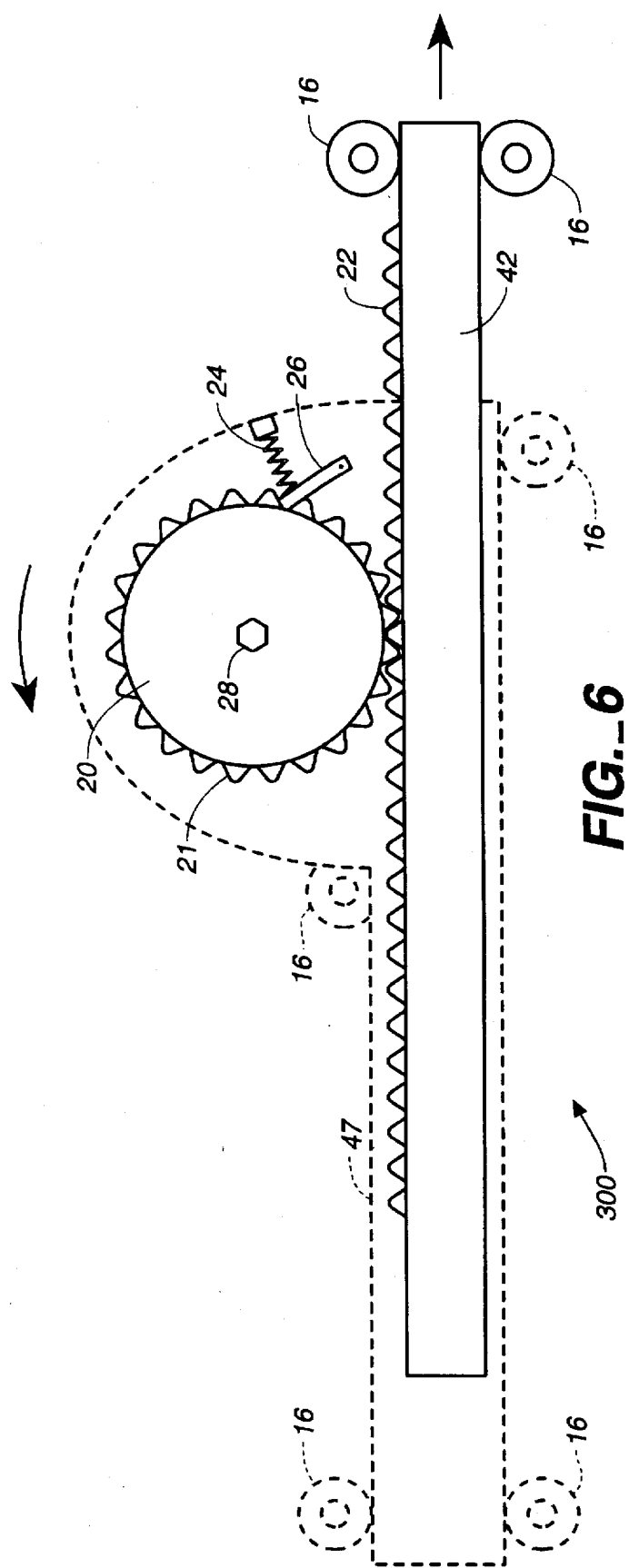
FIG._6

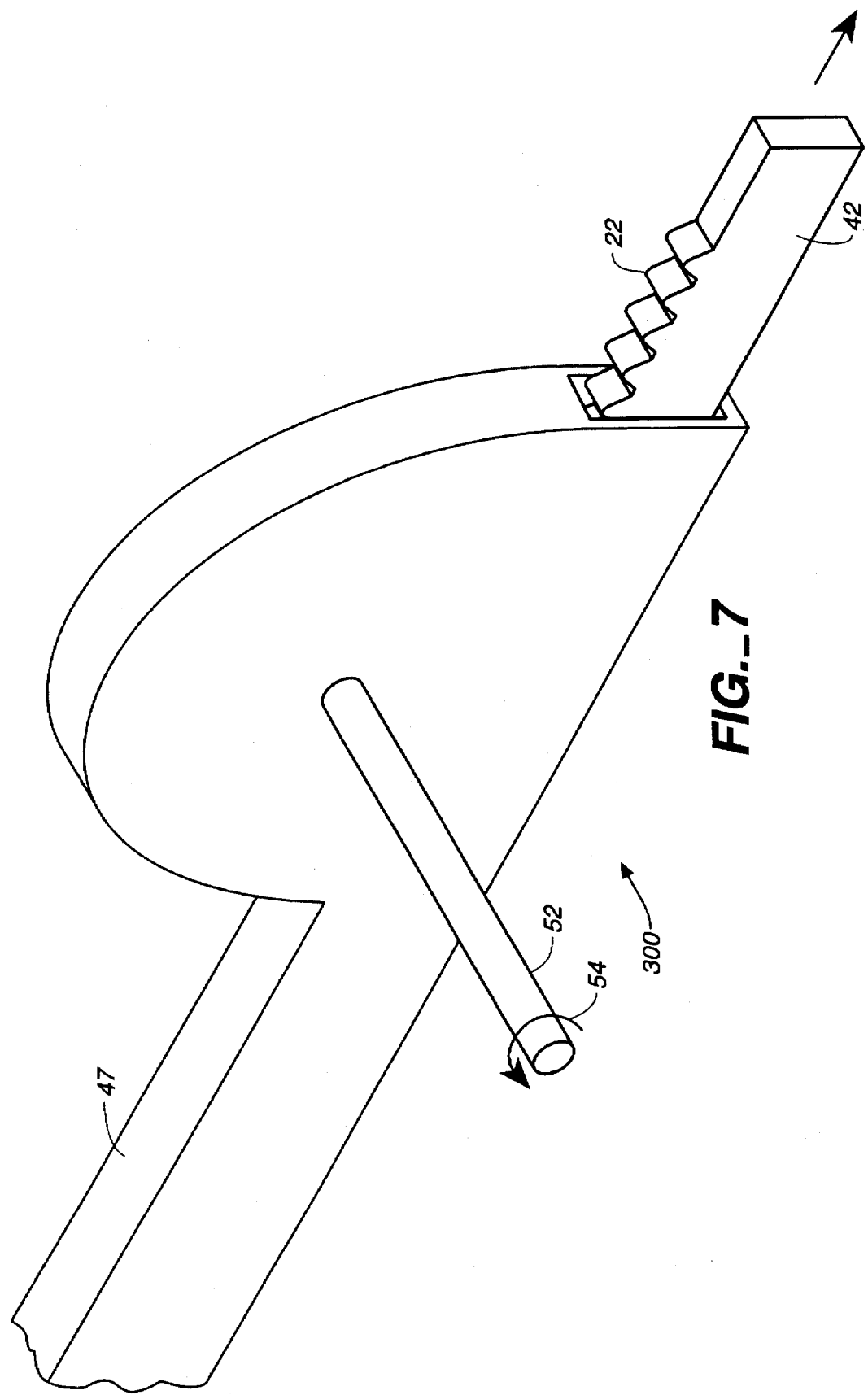
FIG._7

BONE DISTRACTION APPARATUS

BACKGROUND OF THE INVENTION

1. Field of the Invention

The present invention relates generally to a bone distraction apparatus and, more particularly, to an adjustable bone distraction apparatus for use in promoting osteosynthesis.

2. State of the Art

Bones sometimes develop at a different rates, leaving some bones disproportionately shorter than other bones. Alternatively, injury may leave a bone shorter than its original length. Such a condition may lead to difficulties in a patient's movement. For instance, a patient with a shortened tibia may need special shoes for assistance in walking. A small jaw can cause difficulties in chewing or breathing (obstructive sleep apnea). Moreover, deformations are often psychologically distressing to the patient, especially when the deformations occur in craniofacial bones.

One procedure for lengthening bones is referred to as osteosynthesis, osteogenesis, or osteodistraction. According to an osteogenesis procedure, an abnormally short bone is cut into two segments. The two segments are then drawn apart a short distance and secured to a brace that holds the two segments in fixed relationship to each other. New bone then grows in the space between the separated bone segments, and eventually connects the two segments together into a lengthened bone. When the separated bone segments have been fully fused in this manner, the brace may be removed.

Many of the braces employed in osteogenesis procedures are simple mechanical bone fixation devices. Such devices have the shortcoming that they can not easily be adjusted once set. Other bracing devices are known, however, that allow the physician to periodically make adjustments in the brace during the lengthening procedure. For example, a physician may initial set such a brace do that a relatively short gap separates two bone segments. When new bone has filled in the gap between the two segments, the physician may adjust the brace such that the two bone segments are drawn further apart, thereby creating a new gap. After bone has filled in the new gap between the two segments, the physician may once again draw the two segments further apart. This procedure may be repeated as many times as necessary to lengthen the bone appropriately.

Conventional braces used for osteosynthesis are located external to the body. They attach to the bone through pins or screws. While these devices may achieve the desired end result of lengthening the deformed bone, they are unwieldy and unsightly, thereby preventing the user from engaging in many activities during the lengthening procedure. In addition, the mechanical advantage is less since there is a fulcrum effect on the long pins or screws.

This disadvantage has been partly mitigated by the use of implantable bone lengthening devices, as exemplified by U.S. Pat. No. 5,364,396 to Robinson et al. This patent proposes a distraction device comprised of a first and second blocks joined by a threaded drive rod. The first and second blocks are fixed to respective first and second bone segments using bone screws. Rotation of the threaded drive rod causes the first and second blocks (as well as the first and second bone segments) to linearly draw apart from each other. The entire apparatus lies beneath the skin with the exception of a shaft which protrudes from the skin. The shaft provides access to the physician to the subcutaneous drive rod so that the physician can make necessary adjustments.

The device described in the Robinson et al. patent moves bone segments in a linear path. As such, one would expect this device to perform best in lengthening straight bones, such as the tibia or forearm. However, many bones have a more complex curvature, such as the mandible. The device in the Robinson et al. patent is not optimally suited for lengthening such bones having complex curvature.

As an example, FIG. 1 shows the use of a linear distraction device (10) attached to two segments (12 and 14) of a human's mandible bone. As the bone segments are drawn apart, the physician may discover that, due to the natural curvature of the bone, the bone is not being pulled in the desired direction. This may require the physician to surgically remove the device and reposition it, causing added physical trauma to the patient.

Also, Robinson employs a threaded rod—which itself has a number of disadvantages—for drawing the two blocks of his distraction device apart. For instance, the threaded rod provides no locking mechanism for preventing the threaded rod from slipping once adjusted. If the threaded rod does slip, the two blocks may be backward displaced from their originally set position, thereby retarding the bone growth process.

SUMMARY OF THE INVENTION

The present invention, generally speaking, provides a bone distraction device that can be used for any bone, including a bone having a complex curvature, such as the mandible. Further, the present invention provides a bone distraction device which prevents slippage once the device has been adjusted. These and other advantageous results are achieved by providing a bone distraction device that moves two bone segments apart in an arcuate path, instead of a linear path. More particularly, the device includes a curved bar positioned within a housing. The bar is secured to a first bone segment, while the housing is secured to a second bone segment. The bar includes teeth which engage the teeth of a ratchet wheel. Rotation of the ratchet wheel causes the bar to telescopically extend outward in an arcuate path from the housing, thereby separating the first and second bone segments in a arcuate path.

Furthermore, in the preferred embodiment of the present invention, the ratchet wheel includes a pawl which allows the wheel to rotate in a first direction, but prevents the wheel rotating in the opposite direction. The pawl thereby prevents the bar from being displaced in a backward direction once adjusted by the physician.

BRIEF DESCRIPTION OF THE DRAWINGS

The foregoing, and other, objects, features and advantages of the present invention will be more readily understood upon reading the following detailed description in conjunction with the drawings in which:

FIG. 1 shows a prior art application of a distraction device which lengthens craniofacial bones in a linear path.

FIG. 2 shows an exemplary application of the distraction device according to the present invention to lengthen craniofacial bones in an arcuate path.

FIG. 3 shows an exemplary distraction device for moving bone segments in an arcuate path, specifically showing the constituent components of the distraction device.

FIG. 4 shows an exemplary distraction device for moving bone segments in an arcuate path, specifically showing how the device accommodates bars having a variety of curvatures.

FIG. 5 shows the exemplary external appearance of the distraction device illustrated in FIG. 3.

FIG. 6 shows an exemplary distraction device for moving bone segments in a linear path according to the present invention.

FIG. 7 shows the exemplary external appearance of the bone distraction device illustrated in FIG. 6.

DETAILED DESCRIPTION

FIG. 2 shows an exemplary bone distraction device (100) secured to a human's craniofacial skeleton. Unlike the prior art distraction devices, this distraction device is curved to generally match the curvature of the bone segments (12 and 14) it is attached to. Furthermore, the device includes two telescoping members (not shown in FIG. 2) which may be drawn apart in an arcuate path, generally illustrated by the arrow shown in FIG. 2.

FIG. 3 shows an exemplary distraction device (100) for moving bone segments in an arcuate path. Generally, the device consists of a first and second telescoping members, each of which is secured to a respective first and second bone segment. The first member consists of a curved bar (18), preferably having a rectangular cross-section. The bar is telescopically positioned within a second member comprising a housing (34). Both the first and second members are secured to respective first and second bone segments (e.g. portions 12 and 14 in FIG. 2) using bone screws. More particularly, bone screws (not shown) pass through eyelets (16), thereby firmly securing the first and second portions to their respective first and second bone segments. The number and arrangement of eyelets is exemplary. As will be evident to one having ordinary skill in the art, the number of eyelets may be increased or decreased according to the demands of the specific application.

The housing further includes a circular ratchet wheel (20) having teeth (21). The teeth (21) engage corresponding teeth (22) of the bar (18). Accordingly, rotation of the ratchet wheel (20) causes corresponding movement of the bar (18). More specifically, rotation of the ratchet wheel in a counterclockwise direction will cause movement of the bar (18) in an outward arcuate path. The ratchet wheel is rotated by means of a small pin extending perpendicular to the wheel's center (28). The pin (not shown in FIG. 3) extends through the patient's skin, where it is accessible to the physician for making adjustments. Otherwise, the remainder of the apparatus lies beneath the skin. The device is preferably constructed so as to minimize its dimensions in attempt to conceal the existence of the device once implanted.

The device includes a pawl (26) which is hinged at its bottom. A spring (24) keeps the pawl firmly pressed against the teeth (21) of the wheel (20). As shown in FIG. 3, the orientation of the pawl with respect to the teeth of the wheel allows the wheel (20) to move in a counterclockwise direction, but not in a clockwise direction. This prevents the bar (18) from moving backward into the housing once advanced. Although not illustrated in FIG. 3, the device may also include a safety release mechanism to disengage the pawl (26) from the teeth of the wheel to allow the wheel to move in clockwise direction. This would be advantageous in the event that a patient complains of pain after the bar had been advanced several notches. This mechanism would allow the physician to rotate the wheel in a clockwise direction, and thereby alleviate some of the patient's pain.

The bar (18) used in the device of FIG. 2 may have a constant curvature. Alternatively, the curvature of the bar (18) may change. For instance, the bar might have a slight curvature on one end, and a steeper curvature on the opposite end. Generally speaking, the curvature should be chosen to match the curvature of the bone segments the device is attached to. For example, a logarithmic spiral curvature might be appropriate for some bone segments.

In order to accommodate a bar (18) having varying curvatures, the device of FIG. 2 employs two guide rollers (32). The bar (18) is interposed between the guide rollers (32) and the ratchet wheel (20). A tension mechanism (30), such as springs or elastics, hold the guide rollers (32) firmly against the bar (18). The bar (18), in turn, is pressed firmly against the ratchet wheel (20) by the tension mechanism (30).

The guide rollers are fixed to the housing (34), and are preferably free to move in a linear path defined by grooves cut in the housing (34). The location of the grooves as well as the exemplary bounds of motion of the guide rollers (32) are illustrated by arrows (40) in FIG. 5 (which shows the exterior appearance of the distraction device shown in FIG. 3). In operation, the physician turns the ratchet wheel by means of a pin which extends from its center (28). In response thereto, the bar (18) extends outward in an arcuate path. The guide rollers (32) may move up or down as the bar (18) is extended depending on the changing curvature of the bar (18) immediately beneath the ratchet wheel (20).

The guide rollers (32) also offers a great deal of flexibility in accommodating bars (18) of different curvatures. As shown in FIG. 4, the same ratchet wheel assembly can accommodate a bar having a greater curvature, as illustrated by bar (18') shown superimposed (for comparison) on bar (18). To accommodate bar (18'), the guide rollers (32) move upward as shown to a new position (32').

FIG. 5 shows the external appearance of the device of FIG. 3, without a cowling over the rachet bar. Because the device does not use a threaded rod, it can be constructed with a low profile, and thereby allow the device to go virtually unnoticed once attached to the patient's bone beneath the skin. As used herein, profile refers to the dimension of the device perpendicular to both the x and y axes shown in FIG. 5. The device may be constructed of any suitable material, such as stainless steel. Portions of the device may be malleable to further customize the device to bones with varying curvatures.

The low profile ratchet assembly may also be used in a linear distraction device. As illustrated in FIG. 6, the linear distraction device (300) includes two members. The first member includes a linear bar (42), preferably having a rectangular cross-section (as illustrated in FIG. 7). The bar is telescopically positioned within a second member comprising a housing (47). Both the first and second members are secured to respective first and second bone segments (e.g. portions 12 and 14 in FIG. 2) using bone screws. More particularly, bone screws (not shown) pass through eyelets (16), thereby firmly securing the first and second members to their respective first and second bone segments. Again, the number and arrangement of eyelets is only exemplary.

The housing further includes a circular ratchet wheel (20) having teeth (21). The teeth (21) engage corresponding teeth (22) of the bar (42). Accordingly, rotation of the ratchet wheel (20) causes corresponding movement of the bar (42). More specifically, rotation of the ratchet wheel in a counterclockwise direction will cause movement of the bar (42) in an outward linear path. The ratchet wheel is rotated by means of a small pin extending perpendicular to the wheel center (28) (as most clearly illustrated by pin 52 in FIG. 7). The pin (52) extends through the patient's skin, where it is accessible to the physician for making adjustments. Otherwise, the remainder of the apparatus lies beneath the skin.

Similar to the arcuate-path device, the linear device includes a pawl (26) which is hinged at its bottom. A spring (24) keeps the pawl firmly pressed against the teeth (21) of the wheel. As shown in FIG. 6, the orientation of the pawl with respect to the teeth of the wheel allows the wheel (20) to move in a counterclockwise direction, but not in a clockwise direction. This prevents the bar (42) from slipping back once advanced. Although not illustrated in FIG. 6, the device may also include a safety release mechanism to disengage the pawl (26) from the teeth of the wheel to allow the wheel to move in clockwise direction.

The bar (42) does not vary in curvature. As such the linear distraction device may preferably dispense with the guide rollers (32) used in conjunction with the arcuate-path distraction device shown in FIGS. 3 and 4.

In the foregoing description, for purposes of explanation and not limitation, specific details were set forth in order to provide a thorough understanding of the invention. It will be apparent to one of ordinary skill in the art, however, that the present invention may be practiced in other embodiments that depart from these specific details. In other instances, detailed descriptions of well-known methods, devices, and components were omitted so as not to obscure the description of the present invention with unnecessary detail. Furthermore, the above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention as defined by the following claims.

For instance, the device of the present invention may employ a internal power mechanism to turn the ratchet mechanism (as opposed to a manual rotation of the ratchet mechanism via extended pin). Also, ratchet wheel and the bars (18) and (42) may include smaller teeth, and/or teeth having different slopes, shapes and orientations than depicted herein.

What is claimed is:

1. A bone distraction device comprising:
   a first member for attachment to a first bone segment;
   a second member, telescopically interrelated with said first member, for attachment to a second bone segment; and
   a mechanism for moving said first member relative to said second member, wherein movement of said first member relative to said second member defines an arcuate path.

2. The bone distraction device of claim 1, wherein said mechanism for moving further comprises a ratchet wheel.

3. The bone distraction device of claim 2, wherein said ratchet wheel has teeth and said first member has teeth, further wherein said ratchet wheel teeth engage said first member teeth such that rotation of said ratchet wheel causes movement of said first member in said arcuate path.

4. The bone distraction device of claim 3, wherein said mechanism for moving further comprises a pawl in association with said ratchet wheel which prevents the rotation of said ratchet wheel in one direction.

5. The bone distraction device of claim 1, wherein at least one of said first or second members is non-linear.

6. The bone distraction device of claim 5, wherein at least one of said first or second members has a logarithmic curvature.

7. The bone distraction device of claim 1, wherein said mechanism for moving moves said first bone segment away from said second bone segment to promote osteogenesis.

8. A bone distraction device comprising:
   a first member for attachment to a first bone segment;
   a second member, telescopically interrelated with said first member, for attachment to a second bone segment; and
   a mechanism for moving said first member relative to said second member, wherein movement of said first member relative to said second member defines an arcuate path;
   wherein said mechanism for moving includes a ratchet wheel for relatively displacing said first and second members with ratcheted movement; and
   wherein said mechanism for moving further includes at least one guide roller, said at least one guide roller adjustably held in contact with said first member by means of a tension mechanism.

9. The bone distraction device of claim 8, wherein said tension mechanism comprises at least one spring.

* * * * *